United States Patent
Bahn et al.

(10) Patent No.: US 10,527,632 B2
(45) Date of Patent: Jan. 7, 2020

(54) TREATING SCHIZOPHRENIA BASED ON A PANEL OF BIOMARKERS

(75) Inventors: Sabine Bahn, Cambridge (GB); Emanuel Schwarz, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 612 days.

(21) Appl. No.: 13/995,848

(22) PCT Filed: Dec. 20, 2011

(86) PCT No.: PCT/GB2011/052526
§ 371 (c)(1),
(2), (4) Date: Mar. 20, 2014

(87) PCT Pub. No.: WO2012/085555
PCT Pub. Date: Jun. 28, 2012

(65) Prior Publication Data
US 2014/0200151 A1    Jul. 17, 2014

(30) Foreign Application Priority Data

Dec. 20, 2010 (GB) .................................. 1021502.8

(51) Int. Cl.
*G01N 33/68* (2006.01)

(52) U.S. Cl.
CPC ..... *G01N 33/6893* (2013.01); *G01N 33/6896* (2013.01); *G01N 2333/8107* (2013.01); *G01N 2800/302* (2013.01)

(58) Field of Classification Search
CPC ......... G01N 2800/302; G01N 33/6893; G01N 33/6896; G01N 2333/8107
See application file for complete search history.

(56) References Cited

U.S. PATENT DOCUMENTS

| | | | |
|---|---|---|---|
| 6,420,108 | B2 | 7/2002 | Mack et al. |
| 2004/0053292 | A1 | 3/2004 | Tschopp et al. |
| 2006/0099593 | A1 | 5/2006 | Nawa et al. |
| 2008/0020475 | A1 | 1/2008 | Mapes et al. |
| 2009/0175827 | A1 | 7/2009 | Byrom et al. |
| 2011/0165554 | A1 | 7/2011 | Levin et al. |
| 2014/0200151 | A1 | 7/2014 | Bahn et al. |
| 2017/0016921 | A1 | 1/2017 | Bahn et al. |

FOREIGN PATENT DOCUMENTS

| WO | 2008/090319 | 7/2008 |
|---|---|---|
| WO | 2008090319 | 7/2008 |
| WO | 20090077763 | 6/2009 |
| WO | WO 2012/085555 A2 | 6/2012 |

OTHER PUBLICATIONS de Koning et al. Early intervention in patients at ultra high risk of psychosis: benefits and risks. Acta Psychiatr Scand. Jun. 2009; 119(6):426-42. doi: 10.1111/j.1600-0447.2009.01372.x. Epub Mar. 10, 2009.*
Blashki et al, Australian Family Physician, 33(4):221-227, 2004.
Ferguson et al., Mol Neurobiol, 23(2/3):173-185, 2001.
Geddes et al., Biomedical Journal, 321:1371-1376, Dec. 2, 2000.
Nnadi, et al., Individualizing Antipsychotic Drug Therapy in Schizophrenia: The Promise of Pharmacogenertics, Curr Psychology Rep., 9(4):313-318, Aug. 2007.
Pepe, et al., Clinical Chemistry, 52(11):2043-2048, Sep. 21, 2006.
Randox Clinical Chemistry Multisera website, [online] <http://web.archive.org/web/20080915173112/http://www.randox.com/clinical%20chemistry.php>, published online Jun. 2008, retrieved on Oct. 6, 2013.
TC Südhof, J Biol Chem, 277:7692-7632, 2002.
Yokota et al., DNA Research, 10:287-289, 2003.
Bock, "Immunoglobulins, prealbumin, transferrin, albumin, and alpha2-macroglobulin in cerebrospinal fluid and serum in schizophrenic patients", Birth Defects Orig. Artic. Ser., vol. 14, No. 5, pp. 283-295 (1978).
International Search Report from PCT Patent Application No. PCT/GB2011/052523 dated Oct. 29, 2012, application now published as International Publication No. WO2012/085555 on Jun. 28, 2012.
Schwarz et al., "Validation of a blood-based laboratory test to aid in the confirmation of a diagnosis of schizophrenia", Biomarker Insights, vol. 5, pp. 39-47 (2010).
Wong et al., "Acute phase proteins in male Chinese schizophrenic patients in Singapore", Schizophr. Res., vol. 22, No. 2, pp. 165-171 (1996).
Yung, A.R. et al. "Mapping the onset of psychosis: the comprehensive assessment of at-risk mental states", Australian and New Zealand Journal of Psychiatry, vol. 39, pp. 964-971, (2005).
Bromet, E.J. et al., "Long-term diagnostic stability and outcome in recent first-episode cohort studies of schizophrenia", Schizophrenia Bulletin, vol. 31, No. 3, pp. 639-649, (2005).
Fusar-Poli, P. et al., "Predicting psychosis meta-analysis of transition outcomes in individuals at high clinical risk", Arch Gen Psychiatry, vol. 69, No. 3, pp. 220-229, (2012).
Fusar-Poli, P. et al., "Attenuated psychosis syndrome: Ready for DSM-5.1?", Annual Review of Clinical Psychology, vol. 10, pp. 155-192, (2014). van der Gaag, M. et al., "Preventing a first episode of psychosis: Meta-analysis of randomized controlled prevention trials of 12 month and longer-term follow-ups", Schizophrenia Reseach, vol. 149, pp. 56-62, (2013).
Tandon, R., "Definition of psychotic disorders in the DSM-5 too radical, too conservative, or just right!" Schizophrenia Research, vol. 150, pp. 1-2, (2013).
Owens, J., "Funding for accelerating drug development initiative critical", Nature Reviews Drug Discovery, vol. 5, No. 4, p. 271, (2006).
Goodsaid, F. et al., "Implementing the U.S. FDA guidance on pharmacogenomic data submissions", Environmental and Molecular Mutagenesis, vol. 48, No. 5, pp. 354-358, (2007).

(Continued)

*Primary Examiner* — Gregory S Emch
(74) *Attorney, Agent, or Firm* — Evan Law Group LLC (57) ABSTRACT

The invention relates to a method of differential diagnosis of schizophrenia or other psychotic disorder from a further psychiatric disorder.

15 Claims, 3 Drawing Sheets

(56) References Cited

OTHER PUBLICATIONS

Li, Y. et al., "Association between antibodies to multiple infectious and food antigens and new onset schizophrenia among US military personnel", Schizophrenia Research, vol. 151, No. 1-3, pp. 36-42, (2013).
Millikan, A.M. et al., "Evaluation of data obtained from military disability medical administrative databases for service members with schizophrenia or bipolar disorder", Miltary Medicine, vol. 172, No. 10, pp. 1032-1038, (2007).
Schwarz, E. et al., "Identification of a blood-based biological signature in subjects with psychiatric disorders prior to clinical manifestation", The World Journal of Biological Psychiatry, vol. 13, No. 8, pp. 627-632, (2012).
Magaud, E. et al., "Subjects at ultra high risk for psychosis have "heterogeneous" intellectual functioning profile: A multiple-case study", Schizophrenia Research, vol. 152, No. 2-3, pp. 415-420, (2014).
Magaud, E. et al., "Altered semantic but not phonological verbal fluency in young help-seeking individuals with ultra high risk of psychosis", Schizophrenia Research, vol. 123, pp. 53-58, (2010).
Bossuyt, P.M. et al. "Towards complete and accurate reporting of studies of diagnostic accuracy: the STARD initiative", Croatian Medical Journal, vol. 44, No. 5, pp. 635-638, (2003).
Johnson, W.E. et al., "Adjusting batch effects in microarray expression data using empirical bayes methods", Biostatistics, vol. 8, No. 1, pp. 118-127, (2006).
Tibshirani, R., "Regression shrinkage and selection via the lasso", Journal of the Royal Statistical Society, Series B (Methodological), vol. 58, No. 1, pp. 267-288, (1996).
Ruhrmann, S. et al., "Chances and risks of predicting psychosis", European Archives of Psychiatry and Clinical Neuroscience, vol. 262, supplement 2, pp. S85-S90, (2012).
Zarogianni, E. et al., "Towards the identification of imaging biomarkers in schizophrenia, using multivariate pattern classification at a single-subject level", NeuroImage: Clinical, vol. 3, pp. 279-289, (2013).
Schwarz, E. et al., "Identification of subgroups of schizophrenia patients with changes in either immune or growth factor and hormonal pathways", Schizophrenia Bulletin, vol. 40, No. 4, pp. 787-795, (2014).
Domenici, E. et al., "Plasma protein biomarkers for depression and schizophrenia by multi analyte profiling of case-control collections", PLoS One, vol. 5, No. 2, pp. 1-12, (2010).
Miller, B.J. et al., "Meta-analysis of cytokine alterations in schizophrenia: Clinical status and antipsychotic effects", Biological Psychiatry, vol. 70, pp. 663-671, (2011).
Takayanagi, Y. et al., "Relationships between serum leptin level and severity of positive symptoms in schizophrenia", Neuroscience Research, vol. 77, pp. 97-101, (2013).
Li, Y. et al., "Label-free quantitative proteomic analysis reveals dysfunction of complement pathway in peripheral blood of schizophrenia patients: evidence for the immune hypothesis of schizophrenia", Molecular BioSystems, vol. 8, pp. 2664-2671, (2012).
Muller, N. et al., "Anti-inflammatory treatment in schizophrenia", Progress in Neuro-Psychopharmacology & Biological Psychiatry, vol. 42, pp. 146-153, (2013).
Bahn, S. et al., "Challenges of introducing new biomarker products for neuropsychiatric disorders into the market", International Review of Neurobiology, Biomarkers of Neurological and Psychiatric Disease, vol. 101, pp. 299-327, (2011).
International Search Report and written opinion dated May 19, 2015 for PCT application No. PCT/GB2015/050674, 11 pages.
International Preliminary Report on Patentability dated Sep. 13, 2016 for PCT application No. PCT/GB2015/050674, 7 pages.
Schwarz, E. et al., "Validation of a blood-based laboratory test to aid in the confirmation of a diagnosis of schizophrenia", Biomarker Insights, vol. 5, pp. 39-47, (2010).
Bossuyt, P.M. et al., "Towards complete and accurate reporting of studies of diagnostic accuracy: The STARD Initiative", Clinical Chemistry, vol. 49, No. 1, pp. 1-6, (2003).
Benjamini, Y. et al., "Controlling the false discovery rate: A practical and powerful approach to multiple testing", Journal of the Royal Statistical Society, Series B (Methodological), vol. 57, No. 1, pp. 289-300, (1995).
Seaton, B.E. et al., "Sources of heterogeneity in schizophrenia: The role of neuropsychological functioning", Neuropsychology Review, vol. 11, No. 1, pp. 45-67, (2001).
Ferrier, I.N. et al., "Neuropsychological function in euthymic patients with bipolar disorder", British Journal of Psychiatry, vol. 175, pp. 246-251, (1999).
Raja, M. et al., "Asperger's disorder in the emergency psychiatric setting", General Hospital Psychiatry, vol. 23, No. 5, pp. 285-293, (2001).
Fleischhacker, W., "Negative symptoms in patients with schizophrenia with special reference to the primary versus secondary distinction", L'Encephale, Sp. 1, pp. 12-14, (2000).
Riecher-Rossler, A. et al., "Early detection and treatment of schizophrenia: how early?", Acta Psychiatrica Scandinavica, vol. 113, supplemental 429, pp. 73-80, (2006).
Blashki, G. et al, "Managing schizophrenia in general practice", Australian Family Physician, vol. 33, No. 4, pp. 221-227, (2004).
Ferguson, G.D. et al., "Synaptotagmin IV biochemistry, genetics, behavior, and possible links to human is chiatric disease", Molecular Neurobiology, vol. 23, issue 2/3, pp. 173-185, (2001).
Geddes, J. et al., "Atypical antipsychotics in the treatment of schizophrenia: systematic overview and meta-regression analysis", British Medical Journal, vol. 321, pp. 1371-1376, (2002).
Nnadi, C.U. et al., "Individualizing antipsychotic drug therapy in schizophrenia: The promise of pharmacogenetics", Current Psychiatry Reports, vol. 9, issue 4, pp. 313-318, (2007).
Pepe, G. et al., "Lipoprotein(a) in the cerebrospinal fluid of neurological patients with blood-cerebrospinal fluid barrier dysfunction", Clinical Chemistry, vol. 52, No. 11, pp. 2043-2048, (2006).
"Clinical chemistry reagents", Randox, 2 pages, found at web.archive.org/web/20080531145435/http://www.randox.com:80/English/products.cfm?ccs=686 (May 31, 2008), printed on Jun. 13, 2018.
Sudhof, T.C., "Synaptotagmins: Why so many?", The Journal of Biological Chemistry, vol. 277, No. 10, pp. 7629-7632, (2002).
Yokota, H. et al., "Polymorphic 33-bp repeats with promoter-like activity in synaptotagmin 11 gene", DNA Research, vol. 10, pp. 287-289, (2003).
Bock, E. "Immunoglobulins, prealbumin, transferrin, albumin, and alpha2-macroglobulin in cerebrospinal fluid and serum in schizophrenic patients", Birth Defects: Original Article Series, vol. 14, No. 5, pp. 283-295, (1978).
International Search Report and written opinion dated Oct. 29, 2012 for PCT application No. PCT/GB2011/052526, 18 pages.
Doc. No. R1, No. of pp. 9, dated Oct. 29, 2012, PCT/GB2011/052526, PCT.
Doc. No. R2, No. of pp. 9, dated Oct. 29, 2012, PCT/GB2011/052526, PCT.
Doc. No. R10, No. of pp. 8, dated Jul. 31, 2017, U.S. Appl. No. 15/125,069, US.
Doc. No. R11, No. of pp. 7, dated Sep. 19, 2017, U.S. Appl. No. 15/125,069, US.
Doc. No. R12, No. of pp. 4, dated Sep. 21, 2017, 15 710 233.6, EP.
Doc. No. R14, No. of pp. 15, dated Feb. 6, 2018, U.S. Appl. No. 15/125,069, US.
Doc. No. R16, No. of pp. 4, dated May 24, 2018, 15 710 233.6, EP.
U.S. Appl. No. 15/125,069, filed Sep. 9, 2016.

* cited by examiner

TREATING SCHIZOPHRENIA BASED ON A PANEL OF BIOMARKERS

RELATED APPLICATIONS

This application is filed under 35 USC § 371 from PCT Patent Application No. PCT/GB11/052526, which claims priority to previously filed application in the United Kingdom, Serial No. 1021502.8 filed Dec. 20, 2010. The identified previously filed applications are hereby incorporated by reference into the present application.

FIELD OF THE INVENTION

The invention relates to a method of differential diagnosis of schizophrenia or other psychotic disorder from a further psychiatric disorder.

BACKGROUND OF THE INVENTION

Schizophrenia is a psychiatric diagnosis that describes a mental disorder characterized by abnormalities in the perception or expression of reality. It most commonly manifests as auditory hallucinations, paranoid or bizarre delusions, or disorganized speech and thinking with significant social or occupational dysfunction. Onset of symptoms typically occurs in young adulthood, with approximately 0.4-0.6% of the population affected. Diagnosis is based on the patient's self-reported experiences and observed behavior. No laboratory test for schizophrenia currently exists.

Studies suggest that genetics, early environment, neurobiology, psychological and social processes are important contributory factors; some recreational and prescription drugs appear to cause or worsen symptoms. Current psychiatric research is focused on the role of neurobiology, but no single organic cause has been found. Due to the many possible combinations of symptoms, there is debate about whether the diagnosis represents a single disorder or a number of discrete syndromes.

The disorder is thought to mainly affect cognition, but it also usually contributes to chronic problems with behavior and emotion. People with schizophrenia are likely to have additional (comorbid) conditions, including major depression and anxiety disorders; the lifetime occurrence of substance abuse is around 40%. Social problems, such as long-term unemployment, poverty and homelessness, are common. Furthermore, the average life expectancy of people with the disorder is 10 to 12 years less than those without, due to increased physical health problems and a higher suicide rate.

An important utility of biomarkers for psychotic disorders is their response to medication. Administration of antipsychotics remains a subjective process, relying solely on the experience of clinicians. Furthermore, the development of antipsychotic drugs has been based on chance findings often with little relation to the background driving the observations.

Schizophrenia is treated primarily with antipsychotic medications which are also referred to as neuroleptic drugs or neuroleptics. Newer antipsychotic agents such as Clozapine, Olanzapine, Quetiapine or Risperidone are thought to be more effective in improving negative symptoms of psychotic disorders than older medication like Chlorpromazine. Furthermore, they induce less extrapyramidal side effects (EPS) which are movement disorders resulting from antipsychotic treatment.

The history of neuroleptics dates back to the late 19th century. The flourishing dye industry catalyzed development of new chemicals that lay the background to modern day atypical antipsychotics. Developments in anti malaria, antihistamine and anaesthetic compounds also produced various neuroleptics. The common phenomenon to all these processes is a fundamental lack of understanding of the biological mechanisms and pathways that these drugs affect, apart from the observation that they prominently block D2 receptors in the striatum.

There is therefore a pressing need for objective molecular readouts that can diagnose schizophrenia or other psychotic disorders and furthermore indicate whether a patient is responding to medication, as well as for predicting prognosis.

SUMMARY OF THE INVENTION

According to a first aspect of the invention, there is provided the use of one or more analytes selected from: α2 Macroglobulin (A2M), Angiopoietin 2 (ANG2), Betacellulin, Bone morphogenic protein 6 (BMP6), Brain derived neurotrophic factor (BDNF), Carcinoembryonic Antigen (CEA), Epidermal growth factor (EGF), Glutathione S transferase (GST), Haptoglobin (HPT), Interleukin 10 (IL 10), α1 Antitrypsin (α1AT), CD40 Ligand (CD40L), Cortisol, Connective tissue growth factor (CTGF), Eotaxin 3, Factor VII, Follicle stimulating hormone (FSH), GM-CSF, ICAM 1, IGFBP 2, IL 17, IL 5, Luteinizing Hormone (LH), MIF, NrCAM, Pancreatic Polypeptide (PP), Prostatic acid phosphatase (PAP), RANTES (C—C motif chemokine 5), Resistin, SGOT, Sortilin, Stem Cell Factor (SCF), Thrombopoietin (TPO) and Thrombospondin 1 (TSP1) as a biomarker for the differential diagnosis of schizophrenia or other psychotic disorder from a further psychiatric disorder.

According to a second aspect of the invention, there is provided the use of α2 Macroglobulin (A2M), Angiopoietin 2 (ANG2), Betacellulin, Bone morphogenic protein 6 (BMP6), Brain derived neurotrophic factor (BDNF), Carcinoembryonic Antigen (CEA), Epidermal growth factor (EGF), Glutathione S transferase (GST), Haptoglobin (HPT) and Interleukin 10 (IL 10) as a specific panel of analyte biomarkers for the differential diagnosis of schizophrenia or other psychotic disorder from a further psychiatric disorder.

According to a third aspect of the invention, there is provided the use of α2 Macroglobulin (A2M), α1 Antitrypsin (α1AT), Angiopoietin 2 (ANG2), Brain derived neurotrophic factor (BDNF), Betacellulin, Bone morphogenic protein 6 (BMP6), Carcinoembryonic Antigen (CEA), CD40 Ligand (CD40L), Cortisol, Connective tissue growth factor (CTGF), Epidermal growth factor (EGF), Eotaxin 3, Factor VII, Follicle stimulating hormone (FSH), GM-CSF, Glutathione S transferase (GST), Haptoglobin (HPT), ICAM 1, IGFBP 2, Interleukin 10 (IL 10), IL 17, IL 5, Luteinizing Hormone (LH), MIF, NrCAM, Pancreatic Polypeptide (PP), Prostatic acid phosphatase (PAP), RANTES (C—C motif chemokine 5), Resistin, SGOT, Sortilin, Stem Cell Factor (SCF), Thrombopoietin (TPO) and Thrombospondin 1 (TSP1) as a specific panel of analyte biomarkers for the differential diagnosis of schizophrenia or other psychotic disorder from a further psychiatric disorder.

According to a further aspect of the invention, there is provided a method of diagnosing or monitoring schizophrenia or other psychotic disorder, or predisposition thereto, comprising detecting and/or quantifying, in a sample from a test subject, the analyte biomarkers defined herein.

According to a further aspect of the invention, there is provided a method of monitoring efficacy of a therapy in a subject having, suspected of having, or of being predisposed to schizophrenia or other psychotic disorder, comprising detecting and/or quantifying, in a sample from said subject, the analyte biomarkers defined herein.

A further aspect of the invention provides ligands, such as naturally occurring or chemically synthesised compounds, capable of specific binding to the analyte biomarker. A ligand according to the invention may comprise a peptide, an antibody or a fragment thereof, or an aptamer or oligonucleotide, capable of specific binding to the analyte biomarker. The antibody can be a monoclonal antibody or a fragment thereof capable of specific binding to the analyte biomarker. A ligand according to the invention may be labelled with a detectable marker, such as a luminescent, fluorescent or radioactive marker; alternatively or additionally a ligand according to the invention may be labelled with an affinity tag, e.g. a biotin, avidin, streptavidin or His (e.g. hexa-His) tag.

A biosensor according to the invention may comprise the analyte biomarker or a structural/shape mimic thereof capable of specific binding to an antibody against the analyte biomarker. Also provided is an array comprising a ligand or mimic as described herein.

Also provided by the invention is the use of one or more ligands as described herein, which may be naturally occurring or chemically synthesised, and is suitably a peptide, antibody or fragment thereof, aptamer or oligonucleotide, or the use of a biosensor of the invention, or an array of the invention, or a kit of the invention to detect and/or quantify the analyte. In these uses, the detection and/or quantification can be performed on a biological sample such as from the group consisting of CSF, whole blood, blood serum, plasma, urine, saliva, or other bodily fluid, breath, e.g. as condensed breath, or an extract or purification therefrom, or dilution thereof.

Diagnostic or monitoring kits are provided for performing methods of the invention. Such kits will suitably comprise a ligand according to the invention, for detection and/or quantification of the analyte biomarker, and/or a biosensor, and/or an array as described herein, optionally together with instructions for use of the kit.

A further aspect of the invention is a kit for monitoring or diagnosing schizophrenia or other psychotic disorder, comprising a biosensor capable of detecting and/or quantifying the analyte biomarkers as defined herein.

Biomarkers for schizophrenia or other psychotic disorders are essential targets for discovery of novel targets and drug molecules that retard or halt progression of the disorder. As the level of the analyte biomarker is indicative of disorder and of drug response, the biomarker is useful for identification of novel therapeutic compounds in in vitro and/or in vivo assays. Biomarkers of the invention can be employed in methods for screening for compounds that modulate the activity of the analyte.

Thus, in a further aspect of the invention, there is provided the use of a ligand, as described, which can be a peptide, antibody or fragment thereof or aptamer or oligonucleotide according to the invention; or the use of a biosensor according to the invention, or an array according to the invention; or a kit according to the invention, to identify a substance capable of promoting and/or of suppressing the generation of the biomarker.

Also there is provided a method of identifying a substance capable of promoting or suppressing the generation of the analyte in a subject, comprising administering a test substance to a subject animal and detecting and/or quantifying the level of the analyte biomarker present in a test sample from the subject.

BRIEF DESCRIPTION OF THE FIGURES

FIG. 2: Partial Least Squares-Discriminant Analysis (PLS-DA) of SCZ, BPD and Asperger syndrome subjects. PLS-DA using the 34 serum analytes identified as differentially expressed in cohort 1 (SCZ1; see Table 2). Serum samples for SCZ1, SCZ2, SCZ3, BPD and Asperger syndrome were analyzed at the same time using the HumanMAP platform. 34 analytes were identified as differentially expressed in SCZ and these were combined as a single SCZ panel. A) The 34 analyte panel was trained on cohort 1 (SCZ1) and then tested blindly on cohorts 2 and 3 (SCZ2 and SCZ3) using PLS-DA. The triangles indicate true SCZ patients and the plus symbols indicate the true controls. The shaded enclosure approximates the position of the majority of the control population in SCZ 1 and this was maintained for all other cohorts as a reference. The 34 analyte panel was also tested on B) euthymic BPD patients (triangles; cohort 7) and C) Asperger syndrome subjects (triangles; controls=plus symbols; cohort 8). D) The histogram shows the relative contribution of each analyte to the separation achieved in SCZ1. The values are the variable importance in the projection (VIP, determined by SIMCA-P+ software) and the corresponding confidence interval based on a jack-knife procedure. The abbreviations of analytes are as listed in Table 2.

FIG. 3: Partial Least Squares-Discriminant Analysis (PLS-DA) of SCZ and MDD subjects. PLS-DA using the 34 serum analytes identified as differentially expressed in cohort 1 (SCZ1; see Table 2). Serum samples from SCZ4, SCZ5 and MDD subjects were analyzed at the same time using the HumanMAP platform. A) The 34 analyte panel was trained on cohort 4 (SCZ4) and then tested blindly on cohort 5 (SCZ5) using PLS-DA. The triangles indicate true SCZ patients and the plus symbols indicate the true controls. The shaded enclosure approximates the position of the majority of the control population identified for cohort 4 (SCZ4). The 34 analyte panel was also tested on B) MDD patients (triangles; cohort 6). C) The histogram shows the relative contribution of each analyte to the separation achieved in SCZ4 (VIP plot, see legend of FIG. 2). The abbreviations of analytes are as listed in Table 2.

DETAILED DESCRIPTION OF THE INVENTION

The term "biomarker" means a distinctive biological or biologically derived indicator of a process, event, or condition. Analyte biomarkers can be used in methods of diagnosis, e.g. clinical screening, and prognosis assessment and in monitoring the results of therapy, identifying patients most likely to respond to a particular therapeutic treatment, drug screening and development. Biomarkers and uses thereof are valuable for identification of new drug treatments and for discovery of new targets for drug treatment.

It will be readily apparent to the skilled person that the analytes listed herein are known and have been described in the literature.

According to a first aspect of the invention, there is provided the use of one or more analytes selected from: α2 Macroglobulin (A2M), Angiopoietin 2 (ANG2), Betacellulin, Bone morphogenic protein 6 (BMP6), Brain derived neurotrophic factor (BDNF), Carcinoembryonic Antigen (CEA), Epidermal growth factor (EGF), Glutathione S transferase (GST), Haptoglobin (HPT), Interleukin 10 (IL 10), α1 Antitrypsin (α1AT), CD40 Ligand (CD40L), Cortisol, Connective tissue growth factor (CTGF), Eotaxin 3, Factor VII, Follicle stimulating hormone (FSH), GM-CSF, ICAM 1, IGFBP 2, IL 17, IL 5, Luteinizing Hormone (LH), MIF, NrCAM, Pancreatic Polypeptide (PP), Prostatic acid phosphatase (PAP), RANTES (C—C motif chemokine 5), Resistin, SGOT, Sortilin, Stem Cell Factor (SCF), Thrombopoietin (TPO) and Thrombospondin 1 (TSP1) as a biomarker for the differential diagnosis of schizophrenia or other psychotic disorder from a further psychiatric disorder.

The 34 analyte biomarkers of the invention have previously been disclosed in International Patent Application No. PCT/GB2008/004186 along with over 70 other analyte biomarkers for the diagnosis of psychotic disorders such as schizophrenia. The present invention relates to the identification of 34 differentially expressed analytes which gave a separation of 60-75% of schizophrenia subjects from controls across 5 independent cohorts using Partial least squares discriminant analysis. The same analysis also gave a separation of approximately 50% of major depressive disorder (MDD) patients and 10-20% of bipolar disorder (BPD) and Asperger syndrome subjects from controls. These results demonstrate for the first time that a biological signature for schizophrenia can be identified in blood serum. This study lays the groundwork for development of a diagnostic test that can be used as an aid for distinguishing schizophrenia subjects from healthy controls and from those affected by related psychiatric illnesses with overlapping symptoms.

The data presented herein clearly demonstrates the ability of the 34 serum biomarkers to be capable of classifying schizophrenia patients with high sensitivity and specificity compared to control subjects and to patients with other neuropsychiatric disorders.

Therefore, the 34 serum biomarkers provided by the invention is a sensitive and specific predictor for the presence of schizophrenia or other psychotic disorder.

In one embodiment of the invention, the number of analytes comprise any one of the following numbers of analytes: 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more or 20 or more. In general the optimal panel size for the analyte biomarkers of the invention is between 5 and 15.

In one embodiment, the one or more analytes are selected from: α2 Macroglobulin (A2M), Angiopoietin 2 (ANG2), Betacellulin, Bone morphogenic protein 6 (BMP6), Brain derived neurotrophic factor (BDNF), Carcinoembryonic Antigen (CEA), Epidermal growth factor (EGF), Glutathione S transferase (GST), Haptoglobin (HPT) and Interleukin 10 (IL 10).

In one embodiment, the analyte biomarker is selected from α2 Macroglobulin (A2M). Data is presented herein which demonstrates that this biomarker has high levels of statistical significance.

In one embodiment, there is provided a panel of biomarkers which comprises between 5 and 15 of the analytes hereinbefore defined. Thus, according to a second aspect of the invention, there is provided the use of α2 Macroglobulin (A2M), Angiopoietin 2 (ANG2), Betacellulin, Bone morphogenic protein 6 (BMP6), Brain derived neurotrophic factor (BDNF), Carcinoembryonic Antigen (CEA), Epidermal growth factor (EGF), Glutathione S transferase (GST), Haptoglobin (HPT) and Interleukin 10 (IL 10) as a specific panel of analyte biomarkers for the differential diagnosis of schizophrenia or other psychotic disorder from a further psychiatric disorder.

According to a third aspect of the invention, there is provided the use of α2 Macroglobulin (A2M), α1 Antitrypsin (α1AT), Angiopoietin 2 (ANG2), Brain derived neurotrophic factor (BDNF), Betacellulin, Bone morphogenic protein 6 (BMP6), Carcinoembryonic Antigen (CEA), CD40 Ligand (CD40L), Cortisol, Connective tissue growth factor (CTGF), Epidermal growth factor (EGF), Eotaxin 3, Factor VII, Follicle stimulating hormone (FSH), GM-CSF, Glutathione S transferase (GST), Haptoglobin (HPT), ICAM 1, IGFBP 2, Interleukin 10 (IL 10), IL 17, IL 5, Luteinizing Hormone (LH), MIF, NrCAM, Pancreatic Polypeptide (PP), Prostatic acid phosphatase (PAP), RANTES (C—C motif chemokine 5), Resistin, SGOT, Sortilin, Stem Cell Factor (SCF), Thrombopoietin (TPO) and Thrombospondin 1 (TSP1) as a specific panel of analyte biomarkers for the differential diagnosis of schizophrenia or other psychotic disorder from a further psychiatric disorder.

According to a further aspect of the invention, there is provided the use of α2 Macroglobulin (A2M), α1 Antitrypsin (α1AT), Angiopoietin 2 (ANG2), Brain derived neurotrophic factor (BDNF), Betacellulin, Bone morphogenic protein 6 (BMP6), Carcinoembryonic Antigen (CEA), CD40 Ligand (CD40L), Cortisol, Connective tissue growth factor (CTGF), Epidermal growth factor (EGF), Eotaxin 3, Factor VII, Follicle stimulating hormone (FSH), GM-CSF, Glutathione S transferase (GST), Haptoglobin (HPT), ICAM 1, IGFBP 2, Interleukin 10 (IL 10), IL 17, IL 5, Luteinizing Hormone (LH), MIF, NrCAM, Pancreatic Polypeptide (PP), Prostatic acid phosphatase (PAP), RANTES (C—C motif chemokine 5), Resistin, SGOT, Sortilin, Stem Cell Factor (SCF), Thrombopoietin (TPO) and Thrombospondin 1 (TSP1) as a specific panel of biomarkers for the differential diagnosis of schizophrenia or other psychotic disorder from a further psychiatric disorder, such as a neuropsychiatric disorder.

According to a further aspect of the invention, there is provided the use of one or more analytes selected from: α2 Macroglobulin (A2M), α1 Antitrypsin (α1AT), Angiopoietin 2 (ANG2), Brain derived neurotrophic factor (BDNF), Betacellulin, Bone morphogenic protein 6 (BMP6), Carcinoembryonic Antigen (CEA), CD40 Ligand (CD40L), Cortisol, Connective tissue growth factor (CTGF), Epidermal growth factor (EGF), Eotaxin 3, Factor VII, Follicle stimulating hormone (FSH), GM-CSF, Glutathione S transferase (GST), Haptoglobin (HPT), ICAM 1, IGFBP 2, Interleukin 10 (IL 10), IL 17, IL 5, Luteinizing Hormone (LH), MIF, NrCAM, Pancreatic Polypeptide (PP), Prostatic acid phosphatase (PAP), RANTES (C—C motif chemokine 5), Resistin, SGOT, Sortilin, Stem Cell Factor (SCF), Thrombopoietin (TPO) and Thrombospondin 1 (TSP1) as biomarkers for the differential diagnosis of schizophrenia or other psychotic disorder from a further psychiatric disorder, such as a neuropsychiatric disorder.

It will be appreciated that the term "differential diagnosis" refers to the positive diagnosis of schizophrenia or other psychotic disorder from that of a further psychiatric disorder, such as a neuropsychiatric disorder.

Non-limiting examples of psychiatric disorders include: mood disorders such as depression, major depressive disorder, treatment resistant depression, mania, cyclothymic disorder and bipolar disorders (including bipolar disorder in manic, depressive and euthymic phases); anxiety disorders such as generalized anxiety disorder, obsessive-compulsive disorder (OCD), panic attacks and panic disorder, phobic disorders, stress disorders; dissociative disorders such as depersonalization disorder, dissociative amnesia, dissociative fugue, dissociative identity disorder; drug use and dependence; eating disorders such as anorexia nervosa, binge eating disorder and bulimia nervosa; personality disorders; sexuality and sexual disorders such as gender identity disorder and transsexualism and paraphilias; somatoform and factitious disorders such as body dysmorphic disorder, conversion disorder, hypochondriasis, Munchausen syndrome, pain disorder and somatization disorder; Asperger syndrome or suicidal behavior.

In one embodiment, the further psychiatric disorder is selected from one or more of: major depressive disorder (MDD), bipolar disorder (BPD) or Asperger syndrome.

In a further embodiment, the further psychiatric disorder is selected from one or both of bipolar disorder and major depressive disorder.

In one embodiment, one or more of the biomarkers may be replaced by a molecule, or a measurable fragment of the molecule, found upstream or downstream of the biomarker in a biological pathway.

References herein to "other psychotic disorder" relate to any appropriate psychotic disorder according to DSM-IV Diagnostic and Statistical Manual of Mental Disorders, 4th edition, American Psychiatric Assoc, Washington, D.C., 2000. In one particular embodiment, the other psychotic disorder is a psychotic disorder related to schizophrenia. Examples of psychotic disorders related to schizophrenia include brief psychotic disorder delusional disorder, psychotic disorder due to a general medical condition, schizoeffective disorder, schizophreniform disorder, and substance-induced psychotic disorder. In one embodiment, schizophrenia is suitably early onset schizophrenia or first onset schizophrenia.

As used herein, the term "biosensor" means anything capable of detecting the presence of the biomarker. Examples of biosensors are described herein.

Biosensors according to the invention may comprise a ligand or ligands, as described herein, capable of specific binding to the analyte biomarker. Such biosensors are useful in detecting and/or quantifying an analyte of the invention.

Diagnostic kits for the diagnosis and monitoring of schizophrenia or other psychotic disorder are described herein. In one embodiment, the kits additionally contain a biosensor capable of detecting and/or quantifying an analyte biomarker.

Monitoring methods of the invention can be used to monitor onset, progression, stabilisation, amelioration and/or remission.

In methods of diagnosing or monitoring according to the invention, detecting and/or quantifying the analyte biomarker in a biological sample from a test subject may be performed on two or more occasions. Comparisons may be made between the level of biomarker in samples taken on two or more occasions. Assessment of any change in the level of the analyte biomarker in samples taken on two or more occasions may be performed. Modulation of the analyte biomarker level is useful as an indicator of the state of schizophrenia or other psychotic disorder or predisposition thereto. An increase in the level of the biomarker, over time is indicative of onset or progression, i.e. worsening of this disorder, whereas a decrease in the level of the analyte biomarker indicates amelioration or remission of the disorder, or vice versa.

A method of diagnosis or monitoring according to the invention may comprise quantifying the analyte biomarker in a test biological sample from a test subject and comparing the level of the analyte present in said test sample with one or more controls.

The control used in a method of the invention can be one or more control(s) selected from the group consisting of: the level of biomarker analyte found in a normal control sample from a normal subject, a normal biomarker analyte level; a normal biomarker analyte range, the level in a sample from a subject with schizophrenia or other psychotic disorder, or a diagnosed predisposition thereto; schizophrenia or other psychotic disorder biomarker analyte level, or schizophrenia or other psychotic disorder biomarker analyte range.

In one embodiment, there is provided a method of diagnosing schizophrenia or other psychotic disorder, or predisposition thereto, which comprises:
(a) quantifying the amount of the analyte biomarker in a test biological sample; and
(b) comparing the amount of said analyte in said test sample with the amount present in a normal control biological sample from a normal subject.

A higher level of the analyte biomarker in the test sample relative to the level in the normal control is indicative of the presence of schizophrenia or other psychotic disorder, or predisposition thereto; an equivalent or lower level of the analyte in the test sample relative to the normal control is indicative of absence of schizophrenia or other psychotic disorder and/or absence of a predisposition thereto.

The term "diagnosis" as used herein encompasses identification, confirmation, and/or characterisation of schizophrenia or other psychotic disorder, or predisposition thereto. By predisposition it is meant that a subject does not currently present with the disorder, but is liable to be affected by the disorder in time. Methods of monitoring and of diagnosis according to the invention are useful to confirm the existence of a disorder, or predisposition thereto; to monitor development of the disorder by assessing onset and progression, or to assess amelioration or regression of the disorder. Methods of monitoring and of diagnosis are also useful in methods for assessment of clinical screening, prognosis, choice of therapy, evaluation of therapeutic benefit, i.e. for drug screening and drug development.

Efficient diagnosis and monitoring methods provide very powerful "patient solutions" with the potential for improved prognosis, by establishing the correct diagnosis, allowing rapid identification of the most appropriate treatment (thus lessening unnecessary exposure to harmful drug side effects), reducing relapse rates.

Also provided is a method of monitoring efficacy of a therapy for schizophrenia or other psychotic disorder in a subject having such a disorder, suspected of having such a disorder, or of being predisposed thereto, comprising detecting and/or quantifying the analyte present in a biological sample from said subject. In monitoring methods, test samples may be taken on two or more occasions. The method may further comprise comparing the level of the biomarker(s) present in the test sample with one or more control(s) and/or with one or more previous test sample(s) taken earlier from the same test subject, e.g. prior to commencement of therapy, and/or from the same test subject at an earlier stage of therapy. The method may comprise detecting a change in the level of the biomarker(s) in test samples taken on different occasions.

The invention provides a method for monitoring efficacy of therapy for schizophrenia or other psychotic disorder in a subject, comprising:
 (a) quantifying the amount of the analyte biomarker; and
 (b) comparing the amount of said analyte in said test sample with the amount present in one or more control(s) and/or one or more previous test sample(s) taken at an earlier time from the same test subject.

A decrease in the level of the analyte biomarker in the test sample relative to the level in a previous test sample taken earlier from the same test subject is indicative of a beneficial effect, e.g. stabilisation or improvement, of said therapy on the disorder, suspected disorder or predisposition thereto.

Methods for monitoring efficacy of a therapy can be used to monitor the therapeutic effectiveness of existing therapies and new therapies in human subjects and in non-human animals (e.g. in animal models). These monitoring methods can be incorporated into screens for new drug substances and combinations of substances.

Suitably, the time elapsed between taking samples from a subject undergoing diagnosis or monitoring will be 3 days, 5 days, a week, two weeks, a month, 2 months, 3 months, 6 or 12 months. Samples may be taken prior to and/or during and/or following an anti-psychotic therapy. Samples can be taken at intervals over the remaining life, or a part thereof, of a subject.

The term "detecting" as used herein means confirming the presence of the analyte biomarker present in the sample. Quantifying the amount of the biomarker present in a sample may include determining the concentration of the analyte biomarker present in the sample. Detecting and/or quantifying may be performed directly on the sample, or indirectly on an extract therefrom, or on a dilution thereof.

In alternative aspects of the invention, the presence of the analyte biomarker is assessed by detecting and/or quantifying antibody or fragments thereof capable of specific binding to the biomarker that are generated by the subject's body in response to the analyte and thus are present in a biological sample from a subject having schizophrenia or other psychotic disorder or a predisposition thereto.

Detecting and/or quantifying can be performed by any method suitable to identify the presence and/or amount of a specific protein in a biological sample from a patient or a purification or extract of a biological sample or a dilution thereof. In methods of the invention, quantifying may be performed by measuring the concentration of the analyte biomarker in the sample or samples. Biological samples that may be tested in a method of the invention include cerebrospinal fluid (CSF), whole blood, blood serum, plasma, urine, saliva, or other bodily fluid (stool, tear fluid, synovial fluid, sputum), breath, e.g. as condensed breath, or an extract or purification therefrom, or dilution thereof. Biological samples also include tissue homogenates, tissue sections and biopsy specimens from a live subject, or taken post-mortem. The samples can be prepared, for example where appropriate diluted or concentrated, and stored in the usual manner.

Detection and/or quantification of analyte biomarkers may be performed by detection of the analyte biomarker or of a fragment thereof, e.g. a fragment with C-terminal truncation, or with N-terminal truncation. Fragments are suitably greater than 4 amino acids in length, for example 5, 6, 7, 8, 9, 10, 11, 12, 13, 14, 15, 16, 17, 18, 19, or 20 amino acids in length.

The biomarker may be directly detected, e.g. by SELDI or MALDI-TOF. Alternatively, the biomarker may be detected directly or indirectly via interaction with a ligand or ligands such as an antibody or a biomarker-binding fragment thereof, or other peptide, or ligand, e.g. aptamer, or oligonucleotide, capable of specifically binding the biomarker. The ligand may possess a detectable label, such as a luminescent, fluorescent or radioactive label, and/or an affinity tag.

For example, detecting and/or quantifying can be performed by one or more method(s) selected from the group consisting of: SELDI (-TOF), MALDI (-TOF), a 1-D gel-based analysis, a 2-D gel-based analysis, Mass spec (MS), reverse phase (RP) LC, size permeation (gel filtration), ion exchange, affinity, HPLC, UPLC and other LC or LC MS-based techniques. Appropriate LC MS techniques include ICAT® (Applied Biosystems, CA, USA), or iTRAQ® (Applied Biosystems, CA, USA). Liquid chromatography (e.g. high pressure liquid chromatography (HPLC) or low pressure liquid chromatography (LPLC)), thin-layer chromatography, NMR (nuclear magnetic resonance) spectroscopy could also be used.

Methods of diagnosing or monitoring according to the invention may comprise analysing a sample of cerebrospinal fluid (CSF) by SELDI TOF or MALDI TOF to detect the presence or level of the analyte biomarker. These methods are also suitable for clinical screening, prognosis, monitoring the results of therapy, identifying patients most likely to respond to a particular therapeutic treatment, for drug screening and development, and identification of new targets for drug treatment.

Detecting and/or quantifying the analyte biomarkers may be performed using an immunological method, involving an antibody, or a fragment thereof capable of specific binding to the analyte biomarker. Suitable immunological methods include sandwich immunoassays, such as sandwich ELISA, in which the detection of the analyte biomarkers is performed using two antibodies which recognize different epitopes on a analyte biomarker; radioimmunoassays (RIA), direct, indirect or competitive enzyme linked immunosorbent assays (ELISA), enzyme immunoassays (EIA), Fluorescence immunoassays (FIA), western blotting, immunoprecipitation and any particle-based immunoassay (e.g. using gold, silver, or latex particles, magnetic particles, or Q-dots). Immunological methods may be performed, for example, in microtitre plate or strip format.

Immunological methods in accordance with the invention may be based, for example, on any of the following methods.

Immunoprecipitation is the simplest immunoassay method; this measures the quantity of precipitate, which forms after the reagent antibody has incubated with the sample and reacted with the target antigen present therein to form an insoluble aggregate. Immunoprecipitation reactions may be qualitative or quantitative.

In particle immunoassays, several antibodies are linked to the particle, and the particle is able to bind many antigen molecules simultaneously. This greatly accelerates the speed of the visible reaction. This allows rapid and sensitive detection of the biomarker.

In immunonephelometry, the interaction of an antibody and target antigen on the biomarker results in the formation of immune complexes that are too small to precipitate.

However, these complexes will scatter incident light and this can be measured using a nephelometer. The antigen, i.e. biomarker, concentration can be determined within minutes of the reaction.

Radioimmunoassay (RIA) methods employ radioactive isotopes such as $I^{125}$ to label either the antigen or antibody. The isotope used emits gamma rays, which are usually measured following removal of unbound (free) radiolabel. The major advantages of RIA, compared with other immunoassays, are higher sensitivity, easy signal detection, and well-established, rapid assays. The major disadvantages are the health and safety risks posed by the use of radiation and the time and expense associated with maintaining a licensed radiation safety and disposal program. For this reason, RIA has been largely replaced in routine clinical laboratory practice by enzyme immunoassays.

Enzyme (EIA) immunoassays were developed as an alternative to radioimmunoassays (RIA). These methods use an enzyme to label either the antibody or target antigen. The sensitivity of EIA approaches that for RIA, without the danger posed by radioactive isotopes. One of the most widely used EIA methods for detection is the enzyme-linked immunosorbent assay (ELISA). ELISA methods may use two antibodies one of which is specific for the target antigen and the other of which is coupled to an enzyme, addition of the substrate for the enzyme results in production of a chemiluminescent or fluorescent signal.

Fluorescent immunoassay (FIA) refers to immunoassays which utilize a fluorescent label or an enzyme label which acts on the substrate to form a fluorescent product. Fluorescent measurements are inherently more sensitive than colorimetric (spectrophotometric) measurements. Therefore, FIA methods have greater analytical sensitivity than EIA methods, which employ absorbance (optical density) measurement.

Chemiluminescent immunoassays utilize a chemiluminescent label, which produces light when excited by chemical energy; the emissions are measured using a light detector.

Immunological methods according to the invention can thus be performed using well-known methods. Any direct (e.g., using a sensor chip) or indirect procedure may be used in the detection of analyte biomarkers of the invention.

The Biotin-Avidin or Biotin-Streptavidin systems are generic labelling systems that can be adapted for use in immunological methods of the invention. One binding partner (hapten, antigen, ligand, aptamer, antibody, enzyme etc) is labelled with biotin and the other partner (surface, e.g. well, bead, sensor etc) is labelled with avidin or streptavidin. This is conventional technology for immunoassays, gene probe assays and (bio)sensors, but is an indirect immobilisation route rather than a direct one. For example a biotinylated ligand (e.g. antibody or aptamer) specific for an analyte biomarker of the invention may be immobilised on an avidin or streptavidin surface, the immobilised ligand may then be exposed to a sample containing or suspected of containing the analyte biomarker in order to detect and/or quantify an analyte biomarker of the invention. Detection and/or quantification of the immobilised antigen may then be performed by an immunological method as described herein.

The term "antibody" as used herein includes, but is not limited to: polyclonal, monoclonal, bispecific, humanised or chimeric antibodies, single chain antibodies, Fab fragments and $F(ab')_2$ fragments, fragments produced by a Fab expression library, anti-idiotypic (anti-Id) antibodies and epitope-binding fragments of any of the above. The term "antibody" as used herein also refers to immunoglobulin molecules and immunologically-active portions of immunoglobulin molecules, i.e., molecules that contain an antigen binding site that specifically binds an antigen. The immunoglobulin molecules of the invention can be of any class (e.g., IgG, IgE, IgM, IgD and IgA) or subclass of immunoglobulin molecule.

The identification of key biomarkers specific to a disease is central to integration of diagnostic procedures and therapeutic regimes. Using predictive biomarkers appropriate diagnostic tools such as biosensors can be developed; accordingly, in methods and uses of the invention, detecting and quantifying can be performed using a biosensor, microanalytical system, microengineered system, microseparation system, immunochromatography system or other suitable analytical devices. The biosensor may incorporate an immunological method for detection of the biomarker(s), electrical, thermal, magnetic, optical (e.g. hologram) or acoustic technologies. Using such biosensors, it is possible to detect the target biomarker(s) at the anticipated concentrations found in biological samples.

Thus, according to a further aspect of the invention there is provided an apparatus for diagnosing or monitoring schizophrenia or other psychotic disorders which comprises a biosensor, microanalytical, microengineered, microseparation and/or immunochromatography system configured to detect and/or quantify any of the biomarkers defined herein.

The biomarker(s) of the invention can be detected using a biosensor incorporating technologies based on "smart" holograms, or high frequency acoustic systems, such systems are particularly amenable to "bar code" or array configurations.

In smart hologram sensors (Smart Holograms Ltd, Cambridge, UK), a holographic image is stored in a thin polymer film that is sensitised to react specifically with the biomarker. On exposure, the biomarker reacts with the polymer leading to an alteration in the image displayed by the hologram. The test result read-out can be a change in the optical brightness, image, colour and/or position of the image. For qualitative and semi-quantitative applications, a sensor hologram can be read by eye, thus removing the need for detection equipment. A simple colour sensor can be used to read the signal when quantitative measurements are required. Opacity or colour of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Suitably, biosensors for detection of one or more biomarkers of the invention combine biomolecular recognition with appropriate means to convert detection of the presence, or quantitation, of the biomarker in the sample into a signal. Biosensors can be adapted for "alternate site" diagnostic testing, e.g. in the ward, outpatients' department, surgery, home, field and workplace.

Biosensors to detect the biomarkers of the invention include acoustic, plasmon resonance, holographic and microengineered sensors. Imprinted recognition elements, thin film transistor technology, magnetic acoustic resonator devices and other novel acousto-electrical systems may be employed in biosensors for detection of the biomarkers of the invention.

Methods involving detection and/or quantification of the analyte biomarkers of the invention can be performed on bench-top instruments, or can be incorporated onto disposable, diagnostic or monitoring platforms that can be used in a non-laboratory environment, e.g. in the physician's office or at the patient's bedside. Suitable biosensors for performing methods of the invention include "credit" cards with optical or acoustic readers. Biosensors can be configured to allow the data collected to be electronically transmitted to the physician for interpretation and thus can form the basis for e-neuromedicine.

Any suitable animal may be used as a subject non-human animal, for example a non-human primate, horse, cow, pig, goat, sheep, dog, cat, fish, rodent, e.g. guinea pig, rat or mouse; insect (e.g. *Drosophila*), amphibian (e.g. *Xenopus*) or *C. elegans*.

The test substance can be a known chemical or pharmaceutical substance, such as, but not limited to, an anti-psychotic disorder therapeutic; or the test substance can be novel synthetic or natural chemical entity, or a combination of two or more of the aforesaid substances.

There is provided a method of identifying a substance capable of promoting or suppressing the generation of the analyte biomarker in a subject, comprising exposing a test cell to a test substance and monitoring the level of the analyte biomarker within said test cell, or secreted by said test cell.

The test cell could be prokaryotic, however a eukaryotic cell will suitably be employed in cell-based testing methods. Suitably, the eukaryotic cell is a yeast cell, insect cell, *Drosophila* cell, amphibian cell (e.g. from *Xenopus*), *C. elegans* cell or is a cell of human, non-human primate, equine, bovine, porcine, caprine, ovine, canine, feline, piscine, rodent or murine origin.

In methods for identifying substances of potential therapeutic use, non-human animals or cells can be used that are capable of expressing the analyte.

Screening methods also encompass a method of identifying a ligand capable of binding to the analyte biomarker according to the invention, comprising incubating a test substance in the presence of the analyte biomarker in conditions appropriate for binding, and detecting and/or quantifying binding of the analyte to said test substance.

High-throughput screening technologies based on the biomarker, uses and methods of the invention, e.g. configured in an array format, are suitable to monitor biomarker signatures for the identification of potentially useful therapeutic compounds, e.g. ligands such as natural compounds, synthetic chemical compounds (e.g. from combinatorial libraries), peptides, monoclonal or polyclonal antibodies or fragments thereof, which may be capable of binding the biomarker.

Methods of the invention can be performed in array format, e.g. on a chip, or as a multiwell array. Methods can be adapted into platforms for single tests, or multiple identical or multiple non-identical tests, and can be performed in high throughput format. Methods of the invention may comprise performing one or more additional, different tests to confirm or exclude diagnosis, and/or to further characterise a condition.

The invention further provides a substance, e.g. a ligand, identified or identifiable by an identification or screening method or use of the invention. Such substances may be capable of inhibiting, directly or indirectly, the activity of the analyte biomarker, or of suppressing generation of the analyte biomarker. The term "substances" includes substances that do not directly bind the analyte biomarker and directly modulate a function, but instead indirectly modulate a function of the analyte biomarker. Ligands are also included in the term substances; ligands of the invention (e.g. a natural or synthetic chemical compound, peptide, aptamer, oligonucleotide, antibody or antibody fragment) are capable of binding, suitably specific binding, to the analyte.

The invention further provides a substance according to the invention for use in the treatment of schizophrenia or other psychotic disorder, or predisposition thereto.

Also provided is the use of a substance according to the invention in the treatment of schizophrenia or other psychotic disorder, or predisposition thereto.

Also provided is the use of a substance according to the invention as a medicament.

Yet further provided is the use of a substance according to the invention in the manufacture of a medicament for the treatment of schizophrenia or other psychotic disorder, or predisposition thereto.

A kit for diagnosing or monitoring schizophrenia or other psychotic disorder, or predisposition thereto is provided. Suitably a kit according to the invention may contain one or more components selected from the group: a ligand specific for the analyte biomarker or a structural/shape mimic of the analyte biomarker, one or more controls, one or more reagents and one or more consumables; optionally together with instructions for use of the kit in accordance with any of the methods defined herein.

The identification of biomarkers for schizophrenia or other psychotic disorder permits integration of diagnostic procedures and therapeutic regimes. Currently there are significant delays in determining effective treatment and hitherto it has not been possible to perform rapid assessment of drug response. Traditionally, many anti-psychotic therapies have required treatment trials lasting weeks to months for a given therapeutic approach. Detection of an analyte biomarker of the invention can be used to screen subjects prior to their participation in clinical trials. The biomarkers provide the means to indicate therapeutic response, failure to respond, unfavourable side-effect profile, degree of medication compliance and achievement of adequate serum drug levels. The biomarkers may be used to provide warning of adverse drug response. Biomarkers are useful in development of personalized brain therapies, as assessment of response can be used to fine-tune dosage, minimise the number of prescribed medications, reduce the delay in attaining effective therapy and avoid adverse drug reactions. Thus by monitoring a biomarker of the invention, patient care can be tailored precisely to match the needs determined by the disorder and the pharmacogenomic profile of the patient, the biomarker can thus be used to titrate the optimal dose, predict a positive therapeutic response and identify those patients at high risk of severe side effects.

Biomarker-based tests provide a first line assessment of 'new' patients, and provide objective measures for accurate and rapid diagnosis, in a time frame and with precision, not achievable using the current subjective measures.

Furthermore, diagnostic biomarker tests are useful to identify family members or patients at high risk of developing schizophrenia or other psychotic disorder. This permits initiation of appropriate therapy, or preventive measures, e.g. managing risk factors. These approaches are recognised to improve outcome and may prevent overt onset of the disorder.

Biomarker monitoring methods, biosensors and kits are also vital as patient monitoring tools, to enable the physician to determine whether relapse is due to worsening of the disorder, poor patient compliance or substance abuse. If pharmacological treatment is assessed to be inadequate, then therapy can be reinstated or increased; a change in therapy can be given if appropriate. As the biomarkers are sensitive to the state of the disorder, they provide an indication of the impact of drug therapy or of substance abuse.

The following study illustrates the invention.

The Multi-Analyte Profiling (HumanMAP®) platform was used to measure serum concentrations of 189 proteins and small molecules in 250 first and recent onset schizophrenia (SCZ), 35 major depressive disorder (MDD), 32 euthymic bipolar disorder (BPD), 45 Asperger syndrome and 280 control subjects. Preliminary analysis resulted in identification of a signature comprised of 34 analytes in a cohort of closely-matched SCZ (n=71) and control (n=59) subjects. Partial least squares discriminant analysis using this signature gave a separation of 60-75% of SCZ subjects from controls across 5 independent cohorts. The same analysis also gave a separation of approximately 50% of MDD patients and 10-20% of BPD and Asperger syndrome subjects from controls. These results demonstrate for the first time that a biological signature for SCZ can be identified in blood serum. This study lays the groundwork for development of a diagnostic test that can be used as an aid for distinguishing SCZ subjects from healthy controls and from those affected by related psychiatric illnesses with overlapping symptoms.

Methodology

Clinical Samples

The institutional ethical committees approved the protocols of the study, informed written consent was given by all participants and studies were conducted according to the Declaration of Helsinki. All diagnoses were carried out using DSM-IV and clinical tests were performed by psychiatrists under Good Clinical Practice-compliance to minimize variability. The demographic details are shown in Table 1.

the indicated parameters and the medication status of each patient group is also given. Control subjects of cohorts 1 and 7, and those of cohorts 5 and 6 were identical. All controls were recruited from the geographical areas or institutes matching the respective patient populations as indicated for age, gender and social demographics. Controls with a family history of mental disease or with other medical conditions such as type II diabetes, hypertension, cardiovascular or autoimmune diseases were excluded from the study. Schizophrenia subjects with any of these other features were also excluded.

The cohorts used in this study were obtained from multiple centres. Cohorts 1 and 7 were from the University of Cologne, Germany (Ethical Committee of the Medical Faculty of the University of Cologne), cohort 2 from the University of Munster, Germany (Ethics Commission of the Physician Chamber Westphalia Lip and the Medical Faculty of the Westfali Wilhelm University Münster), cohorts 3, 5 and 6 from the University of Magdeburg, Germany (Ethics committee of the Medical Faculty of the University of Magdeburg), cohort 4 from Erasmus University, Netherlands (Research Ethics Committee of the Erasmus Medical Centre) and cohort 8 from the Department of Psychiatry, University of Cambridge, UK (Cambridge Research Ethics Committee). Cohorts 1-5 were the same as those reported recently (Schwarz E et al 2010 *Biomark Insights;* 5: 39-47).

Blood samples were collected from all subjects into S-Monovette 7.5 mL serum tubes (Sarstedt; Numbrecht, Germany). Serum was prepared by placing samples at room temperature for 2 hours for blood coagulation, followed by centrifugation at 4,000×g for 5 minutes. The resulting supernatants were stored at −80° C. in Low Binding Eppendorf tubes (Hamburg, Germany) prior to analysis.

TABLE 1

Demographic Details of Participants

|  | 1 SCZ1 | 2 SCZ2 | 3 SCZ3 | 4 SCZ4 | 5 SCZ5 | 6 MDD | 7 BPD | 8 Asperger |
|---|---|---|---|---|---|---|---|---|
| Patients (n) | 71 | 46 | 46 | 47 | 40 | 35 | 32 | 45 |
| Controls (n) | 59 | 46 | 45 | 40 | 40 | 40 | 59 | 50 |
| Patients (M/F) | 42/29 | 35/11 | 30/16 | 36/11 | 27/12 | 13/22 | 13/19 | 22/23 |
| Controls (M/F) | 31/28 | 35/11 | 27/18 | 33/7 | 26/14 | 26/14 | 31/28 | 26/24 |
| Patients Age | 31 ± 10 | 27 ± 9 | 35 ± 12 | 26 ± 8 | 35 ± 10 | 40 ± 14 | 34 ± 10 | 32 ± 9 |
| Controls Age | 30 ± 8 | 27 ± 9 | 34 ± 12 | 27 ± 4 | 36 ± 11 | 36 ± 11 | 30 ± 8 | 32 ± 7 |
| Patients BMI | 24 ± 5 | 22 ± 2 | 26 ± 5 | na | 25 ± 5 | 25 ± 7 | 25 ± 4 | na |
| Controls BMI | 23 ± 4 | na | 24 ± 4 | na | 24 ± 3 | 24 ± 3 | 23 ± 4 | na |
| Patients Smoking (y/n/na) | 25/23/23 | 16/26/4 | 25/21/0 | 33/14/0 | 22/18/0 | 17/18/0 | 7/14/11 | 11/34/0 |
| Controls Smoking (y/n/na) | 25/34/0 | na | 11/34/0 | na | 18/22/0 | 18/22/0 | 25/34/0 | 9/41/0 |
| Patients *Cannabis* (y/n/na) | 33/22/16 | 15/27/4 | 8/38/0 | 23/24/0 | na | na | 14/7/11 | 2/20/23 |
| Controls *Cannabis* (y/n/na) | 31/25/3 | na | 0/45/0 | na | na | na | 31/25/3 | 2/39/9 |
| Medication free patients | all | all | 33/45 | all | all | all | 4/32 | 36/45 |

M/F = male/female, BMI = body mass index, Y/N = yes/no, na = not available. Values are shown as mean ± sd. Control groups of cohorts 1 and 7, and those of cohorts 5 and 6 were identical.

Subjects in cohorts 1-5 were diagnosed as having the paranoid subtype of SCZ (295.30). All SCZ patients from cohort 1, 2, 4 and 5 and 33 out of 45 patients from cohort 3 were drug naïve at the time of sample collection. The patients in cohort 6 were acutely ill with MDD and were either drug-naïve (n=22) or drug-free (n=13) for at least 6 weeks prior to sample collection. The subjects in cohort 7 were diagnosed as euthymic BPD type I (296.4) and type II (296.89). The individuals in Cohort 8 were diagnosed as having Asperger syndrome. All subjects were matched for Multiplexed Immunoassay The HumanMAP® multiplexed antigen immunoassay platform comprising 189 analytes was used to measure the concentrations of serum proteins and small molecules in a Clinical Laboratory Improvement Amendments (CLIA)-certified laboratory at Rules Based Medicine (www.rulesbasedmedicine.com) as described previously (Schwarz E et al 2010 *Biomark Insights;* 5: 39-47). Samples were randomized and blinded by code numbers until all biochemical assays were completed. Assays were calibrated using standards, raw intensity measurements converted to absolute protein concentrations by comparison to the standards, and performance was verified using quality control samples. Data analyses were performed using the statistical software package R (http://wwws-project.org).

The protocol for the study participants, clinical samples and test methods was carried out in compliance with the Standards for Reporting of Diagnostic Accuracy (STARD) initiative (Bossuyt P M et al *Clin Chem* 2003 January; 49(1): 1-6).

Data Analyses

Univariate analyses were carried out to identify significant differences in expression of analytes between patients and controls using a two-tailed non-parametric Wilcoxon Rank sum test. Analysis of covariance (ANCOVA) was carried out on log-transformed data to assess the effect of demographic variables such as age, gender and BMI on the significance of identified marker candidates. P-values of less than 0.05 were considered to indicate statistical significance. The false discovery rate was controlled according to (Benjamini and Hochberg (Benjamini Y, Hochberg Y. *J Roy Statist Soc Ser B* 1995; 57: 289-300). Multivariate analysis was carried out using SIMCA P+ 10.5 (Umetrics; Umea, Sweden) for partial least squares discriminant analysis (PLS-DA) to visualize any separation between patient and control subjects as indicated.

Results

Identification of Preliminary SCZ Biomarker Signature

The first stage of the study was aimed at identification of differentially expressed serum analytes in a single cohort of first onset anti-psychotic naive SCZ subjects and well-matched controls using the HumanMAP analysis. Cohort 1 was chosen for this analysis since this group was comprised of SCZ (n=71) and controls (n=59) who were matched for age, gender, body mass index, smoking, cannabis consumption and date of sample collection (Table 1). This analysis resulted in identification of 34 analytes which were altered significantly in SCZ compared to control subjects using unpaired two-tailed Wilcoxon Rank Sum tests and remained significant after adjusting for covariates using ANCOVA (Table 2).

TABLE 2

Identification of differentially expressed serum analytes in cohort 1 (SCZ 1) subjects using HumanMAP ® analysis

| Analyte | p-value | q-value | FC |
|---|---|---|---|
| α1 Antitrypsin (a1AT) | 0.005* | 0.032 | 1.08 |
| α2 Macroglobulin (A2M) | <0.001 | 0.001 | 1.21 |
| Angiopoietin 2 (ANG2) | <0.001 | 0.008 | 1.33 |
| Brain derived neurotrophic factor (BDNF) | 0.004* | 0.027 | 0.87 |
| Betacellulin | <0.001 | 0.012 | 1.93 |
| Bone morphogenic protein 6 (BMP6) | <0.001 | 0.007 | 2.02 |
| Carcinoembryonic Antigen (CEA) | 0.001 | 0.002 | 1.75 |
| CD40 Ligand (CD40L) | 0.028 | 0.012 | 0.64 |
| Cortisol | 0.003 | 0.036 | 1.14 |
| Connective tissue growth factor (CTGF) | 0.003 | 0.046 | 1.17 |
| Epidermal growth factor (EGF) | <0.001 | <0.001 | 0.49 |
| Eotaxin 3 | 0.002 | 0.029 | 2.12 |
| Factor VII | 0039* | 0.144 | 0.87 |
| Follicle stimulating hormone (FSH) | 0.001 | 0.062 | 2.41 |
| GM-CSF | 0.002 | 0.109 | 0.91 |
| Glutathione S transferase (GST) | <0.001* | <0.001 | 1.30 |
| Haptoglobin (HPT) | <0.001* | 0.002 | 1.68 |
| ICAM 1 | 0.001 | 0.149 | 0.94 |
| IGFBP 2 | 0.045* | 0.149 | 1.22 |

TABLE 2-continued

Identification of differentially expressed serum analytes in cohort 1 (SCZ 1) subjects using HumanMAP ® analysis

| Analyte | p-value | q-value | FC |
|---|---|---|---|
| Interleukin 10 (IL 10) | <0.001 | <0.001 | 1.21 |
| IL 17 | <0.001* | <0.001 | 1.62 |
| IL 5 | 0.001* | 0.010 | 0.72 |
| Luteinizing Hormone (LH) | <0.001 | 0.015 | 1.66 |
| MIF | 0.024 | 0.149 | 1.72 |
| NrCAM | 0.001 | 0.149 | 0.83 |
| Pancreatic Polypeptide (PP) | <0.001 | 0.008 | 1.64 |
| Prostatic acid phosphatise (PAP) | 0.001 | 0.036 | 0.82 |
| RANTES (C-C motif chemokine 5) | 0.005 | 0.121 | 1.17 |
| Resistin | 0.007 | 0.027 | 0.80 |
| SGOT | 0.008 | 0.005 | 1.25 |
| Sortilin | <0.001 | <0.001 | 0.76 |
| Stem Cell Factor (SCF) | 0.033 | 0.149 | 0.93 |
| Thrombopoietin (TPO) | 0.004 | 0.005 | 0.84 |
| Thrombospondin 1 (TSP1) | 0.014 | 0.002 | 0.82 |

FC = fold change (average intensity of analyte in SCZ divided by the average intensity in controls of cohort 1).
p-values were calculated using ANCOVA based on SCZ patients and controls in cohort 1 (gender, age, BMI, smoking and *cannabis* consumption used as covariates),
*Diagnosis-covariate interaction was significant and p-value was determined using non-parametric Wilcoxon Rank sum test instead.
q values represent FDR adjusted p-values derived from Wilcoxon Rank sum tests comparing SCZ patients and controls in cohort 1
GM-CSF = granulocyte macrophage colony stimulating factor, IGFBP2 = insulin-like growth factor binding protein 2, MIF = macrophage migration inhibitory factor, SGOT = serum glutamic oxaloacetic transaminase.

The majority of these analytes were also significant after controlling the false discovery rate. Analytes showing the highest magnitude fold-changes were betacellulin, bone morphogenic protein 6 (BMP6), eotaxin 3, follicle stimulating hormone (FSH) and epidermal growth factor (EGF), which were all altered by approximately 2-fold in SCZ compared to control subjects. For added confirmation of the results, the same serum samples were re-assayed approximately 3 months after the first analysis. This repeat analysis showed good reproducibility of the results with an average correlation across all analytes of 0.81 (Pearson's correlation coefficient) and 50% of the analytes had a correlation greater than 0.90 (data not shown).

Figure 1:
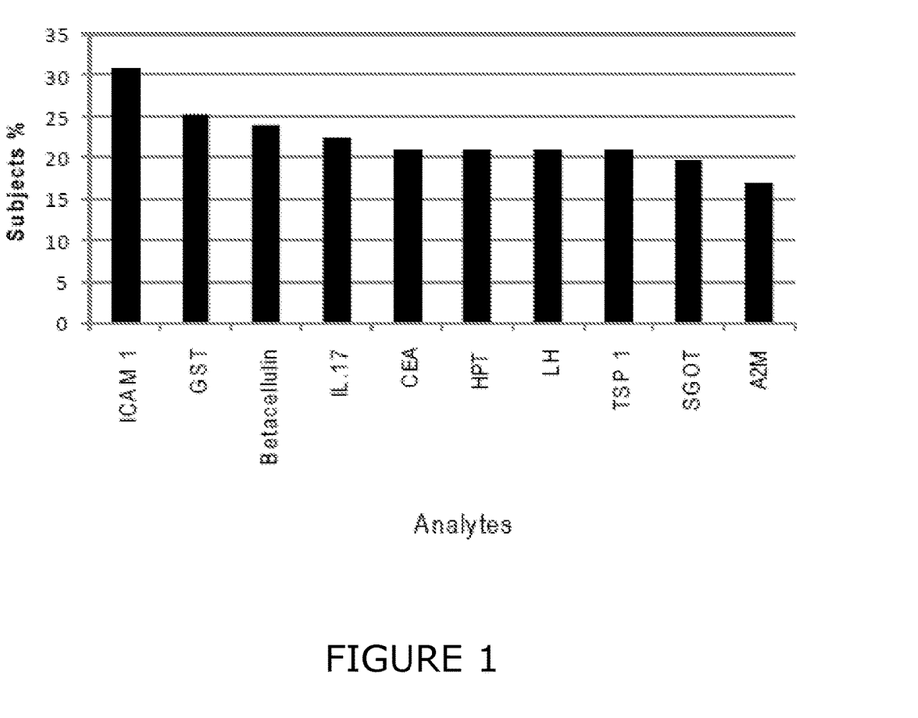
FIG. 1: Biomarkers changed in more than 15% of individual patients. The y axis indicates the percentage of subjects in which these biomarkers were altered cohort 1. Differential expression was determined by identifying biomarkers that showed measurements varying by more than two standard deviations in individual SCZ patients compared to the mean control value in the same cohort. The abbreviations are as indicated in the legend for Table 2.

The proportion of subjects in which these biomarkers were altered across in cohort 1 was also determined. In this case, differential expression of a biomarker in a subject was indicated if the measurement varied by more than two standard deviations compared to that of the mean control measurement in the same cohort. Using these criteria, ICAM 1, GST, Betacellulin, GST and IL 17 were altered in the highest proportion of subjects (FIG. 1).

Validation of SCZ Signature in Other Cohorts

Figure 2:
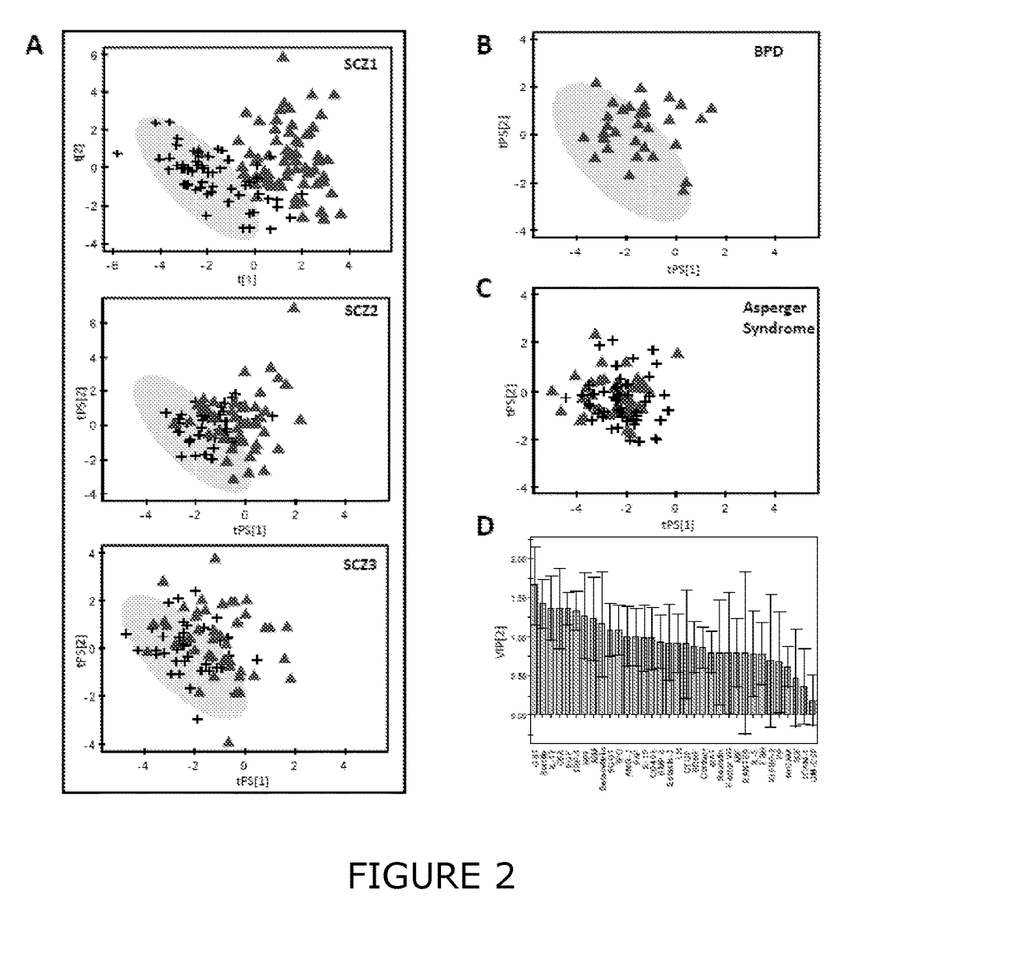

One factor which renders diagnosis of SCZ imprecise is the heterogeneous nature of the disease and the overlap of SCZ symptoms with those of other psychiatric conditions (Seaton B E et al 2001 March; 11(1): 45-67). In the next phase of the study, the 34 differentially expressed analytes identified in cohort 1 were tested as a combined panel using samples from SCZ and control subjects in the first 3 cohorts (SCZ1, SCZ2 and SCZ3) and in cohorts 7 (BPD) and 8 (Asperger syndrome) since these were profiled using HumanMAP analysis at the same time. PLS-DA was used to visualize any separation between patient and control subjects. This showed the 34-analyte panel resulted in a separation of SCZ patients from controls by 40-85% across cohorts 1-3 (FIG. 2A). For comparison, euthymic BPD patients were tested as such patients can experience disruptions in cognitive behaviours as seen in SCZ (Ferrier I N et al *Br J Psychiatry* 1999 September; 175: 246-251). Asperger syndrome subjects (cohort 8) were analyzed since they can also show overlap with SCZ in display of such symptoms as emotional lability, anxiety and poor social functioning (Raja M, Azzoni A. *Gen Hosp Psychiatry* 2001 September-October; 23(5): 285-293). In contrast to SCZ, the signature resulted in little or no separation of BPD patients (FIG. 2B) or Asperger syndrome subjects (FIG. 2C) from the respective controls. The analytes most important for the separation achieved in cohort 1 were GST, sortilin, IL17, CEA, EGF, TSP1, HPT, A2M, Betacellulin, SGOT, TPO and ANG2 in descending order (FIG. 2D). It should be noted that the separation achieved in SCZ1 reflects the training performance of the multivariate model and is positively-biased as data from this cohort were used to establish the initial 34 analyte signature.

Figure 3:
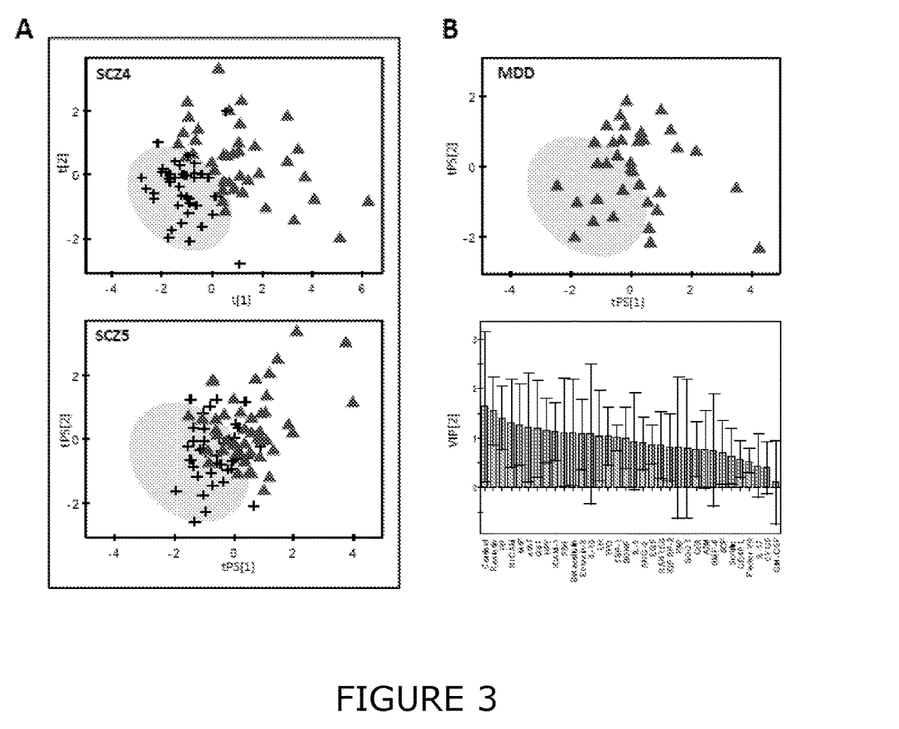

In addition, the 34 analyte panel was trained on cohort 4 (SCZ4) and tested on cohorts 5 (SCZ5) and 6 (MDD) since these samples were subjected to HumanMAP analysis at the same time. Classification of subjects using the panel showed a separation of 60-75% of SCZ patients from control subjects in cohorts 4 and 5 (FIG. 3A). As before, the separation displayed for cohort 4 (SCZ4) represents the training performance of the multivariate model. MDD subjects were chosen for the comparative disease analysis due to the overlap of negative symptoms between this disorder and schizophrenia (Fleischhacker W. *Encephale* 2000 October; 26 Spec No 1: 12-14). Approximately 50% of MDD patients also showed a separation from controls (FIG. 3B). This suggested that the panel may not be entirely specific for SCZ. The most significant analytes for the separation achieved in cohort 4 were cortisol, resistin, PP, NrCAM, MIF, A1AT, GST, HPT and ICAM 1 in descending order (FIG. 3C).

Figure 4:
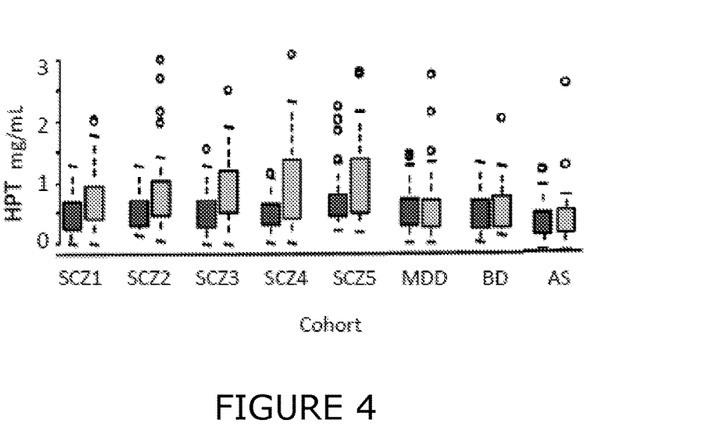
FIG. 4: Altered Expression of Haptoglobin (HPT) across SCZ Cohorts. Expression profile changes of HPT in patient and control populations across the SCZ and non-SCZ cohorts. The expression levels are given as box plots for patients (pale grey) and controls (dark grey).

An example of the biological profile of HPT is given which shows significant alterations in all of the SCZ cohorts and no change in the any of the non-SCZ conditions (FIG. 4). These findings show that some components of the 34 analyte biomarker panel was relatively specific for SCZ.

DISCUSSION

The results described herein demonstrate for the first time that a reproducible biological signature for SCZ can be identified in blood serum. One strong point of the current investigation is that samples were obtained from first onset antipsychotic naïve subjects who were well-matched with controls for factors such as age, gender, substance abuse and lifestyle. This was an important consideration to maximize the capability of identifying molecular biomarkers associated with the disease and minimize the chances of identifying those associated with potential confounding factors. Most previous SCZ studies have investigated chronic patients who have been treated with antipsychotic medications and who often have multiple co-morbidities, which can confound the results of biomarker investigations. Domenici et al recently described the identification of SCZ and MDD biomarkers, although the majority of the samples used for this study came from treated subjects (Domenici E et al. 2010 *PLoS One;* 5(2): e9166). Studies involving first onset antipsychotic naïve patients are scarce due to the fact that even large psychiatric centres can only enlist around 20-30 of these subjects each year and few centres follow strict standard operating procedures for collection of samples. This problem was overcome by obtaining samples from first onset antipsychotic naïve and minimally-treated SCZ patients from multiple clinical centres over a 10-year time span. All of the patients and controls underwent extensive clinical characterization, and sera were collected and stored according to strict standard operating procedures. In addition, all protocols involving clinical subjects, samples and test measurements were carried out in compliance with the Standards for Reporting of Diagnostic Accuracy (STARD) initiative (Bossuyt P M et al. *Clin Chem* 2003 January; 49(1): 1-6) to maximize reliability and accuracy of the results.

A significant increase in cortisol levels was found across all SCZ cohorts and a non-significant trend for increase across all other non-SCZ cohorts (p=0.188–0.268).

In summary, the claimed biomarker signature has provided potential additional insights into the biological pathways underlying the onset or development of SCZ. In addition, the signature also shows potential in the development of a test for distinguishing SCZ patients from controls and from subjects with other psychiatric disorders.

These results highlight the importance of evaluating biomarkers in larger studies with explicit assessment of the ability to classify subjects. The future success of biomarker strategies may depend on the discovery of new molecules to complement the most robust existing biomarkers, perhaps with the help of state-of-the-art targeted and non-targeted approaches. In addition, it should be noted that tests for disorders with a low incidence such as SCZ require exceptionally high specificities if used in the general population. For this reason, the most effective use of such tests would be as a confirmatory diagnostic aid by a psychiatric specialist in conjunction with a clinical assessment. In this way, the test would be used in populations already enriched for schizophrenia with the purpose of establishing and confirming a diagnosis more rapidly, as compared to the requirement for 6 months duration of continuous symptoms using the current DSM IV-based diagnosis. Such an application of a biomarker test would help to initiate treatment of patients more rapidly and, therefore, reduce the duration of untreated psychosis and, in turn, improve patient outcomes (Riecher-Rossler A et al *Acta Psychiatr Scand Suppl* 2006; (429): 73-80). This would be an important breakthrough by helping clinical psychiatrists to identify vulnerable patients early in the disease process, allowing for earlier or even preventative therapeutic intervention.

The invention claimed is:

1. A method of treating an individual suspected of suffering from schizophrenia, or a predisposition thereto, comprising:
   a) obtaining a biological sample of an individual with a psychiatric disorder who has not been diagnosed with schizophrenia;
   b) quantifying concentrations of a panel of biomarkers in the biological sample by subjecting the sample to SELDI (-TOF) spectrometry, MALDI (-TOF) spectrometry, a 1-D gel-based analysis, a 2-D gel-based analysis, mass spectrometry (MS), liquid chromatography (LC), reverse phase liquid chromatography (RP-LC), size permeation chromatography, gel filtration chromatography, ion exchange chromatography, affinity chromatography, FPLC, HPLC, UPLC, other LC-based techniques, other LC-MS-based techniques, or combinations thereof; or
   an immunological method, a biosensor method, a microanalytical method, a microengineered method, a microseparation method, an immunochromatography method, or combinations thereof;
   and
   c) administering an antipsychotic agent to the individual showing a biomarker profile having a higher level of a set of biomarkers from the panel as compared to a normal control, wherein the set of biomarkers consists of α2 Macroglobulin (A2M), α1 Antitrypsin (α1AT), Angiopoietin 2 (ANG2), Brain derived neurotrophic factor (BDNF), Betacellulin, Bone morphogenic protein 6 (BMP6), Carcinoembryonic Antigen (CEA), CD40 Ligand (CD40L), Cortisol, Connective tissue growth factor (CTGF), Epidermal growth factor (EGF), Eotaxin 3, Factor VII, Follicle stimulating hormone (FSH), GM-CSF, Glutathione S transferase (GST), Haptoglobin (HPT), ICAM 1, IGFBP 2, Interleukin 10 (IL 10), IL 17, IL 5, Luteinizing Hormone (LH), MIF, NrCAM, Pancreatic Polypeptide (PP), Prostatic acid phosphatise (PAP), RANTES (C—C motif chemokine 5), Resistin, SGOT, Sortilin, Stem Cell Factor (SCF), Thrombopoietin (TPO) and Thrombospondin 1 (TSP1).

2. The method of claim 1, wherein the quantifying is performed on two or more occasions.

3. The method of claim 2, wherein the quantifying is performed prior to the administering.

4. The method of claim 2, wherein the quantifying is repeated at intervals throughout the individual's lifetime.

5. The method of claim 1, wherein the administering further comprises at least one therapy selected from the group consisting of psychotherapy, counseling, hospitalization, electroconvulsive therapy, and combinations thereof.

6. A method of treatment comprising:
a) obtaining a biological sample of an individual with a psychiatric disorder having symptoms of bipolar disorder, Asperger syndrome, or major depressive disorder that overlap with schizophrenia and who has not been diagnosed with schizophrenia; and
b) quantifying concentrations of a panel of biomarkers in the biological sample by subjecting the sample to SELDI (-TOF) spectrometry, MALDI (-TOF) spectrometry, a 1-D gel-based analysis, a 2-D gel-based analysis, mass spectrometry (MS), liquid chromatography (LC), reverse phase liquid chromatography (RP-LC), size permeation chromatography, gel filtration chromatography, ion exchange chromatography, affinity chromatography, FPLC, HPLC, UPLC, other LC-based techniques, other LC-MS-based techniques, or combinations thereof; or
an immunological method, a biosensor method, a microanalytical method, a microengineered method, a microseparation method, an immunochromatography method, or combinations thereof;
(c) administering an antipsychotic agent to the individual showing a biomarker profile having a higher level of a set of biomarkers from the panel as compared to a normal control;
wherein the set of biomarkers consists of α2 Macroglobulin (A2M), α1 Antitrypsin (α1AT), Angiopoietin 2 (ANG2), Brain derived neurotrophic factor (BDNF), Betacellulin, Bone morphogenic protein 6 (BMP6), Carcinoembryonic Antigen (CEA), CD40 Ligand (CD40L), Cortisol, Connective tissue growth factor (CTGF), Epidermal growth factor (EGF), Eotaxin 3, Factor VII, Follicle stimulating hormone (FSH), GM-CSF, Glutathione S transferase (GST), Haptoglobin (HPT), ICAM 1, IGFBP 2, Interleukin 10 (IL 10), IL 17, IL 5, Luteinizing Hormone (LH), MIF, NrCAM, Pancreatic Polypeptide (PP), Prostatic acid phosphatise (PAP), RANTES (C—C motif chemokine 5), Resistin, SGOT, Sortilin, Stem Cell Factor (SCF), Thrombopoietin (TPO) and Thrombospondin 1 (TSP1).

7. The method of claim 6, wherein the quantifying is performed on two or more occasions.

8. The method of claim 7, wherein the quantifying is performed prior to the administering.

9. The method of claim 7, wherein the quantifying is repeated at intervals throughout the individual's lifetime.

10. The method of claim 6, wherein the administering further comprises at least one therapy selected from the group consisting of psychotherapy, counseling, hospitalization, electroconvulsive therapy, and combinations thereof.

11. A method of treatment comprising:
a) obtaining a biological sample of an individual who displays symptoms of a psychiatric disorder that has overlapping symptoms with schizophrenia and has not been diagnosed with schizophrenia;
b) quantifying concentrations of a panel of biomarkers in the biological sample by subjecting the sample to SELDI (-TOF) spectrometry, MALDI (-TOF) spectrometry, a 1-D gel-based analysis, a 2-D gel-based analysis, mass spectrometry (MS), liquid chromatography (LC), reverse phase liquid chromatography (RP-LC), size permeation chromatography, gel filtration chromatography, ion exchange chromatography, affinity chromatography, FPLC, HPLC, UPLC, other LC-based techniques, other LC-MS-based techniques, or combinations thereof; or
an immunological method, a biosensor method, a microanalytical method, a microengineered method, a microseparation method, an immunochromatography method, or combinations thereof;
(c) administering an antipsychotic agent to the individual showing a biomarker profile having a higher level of a set of biomarkers from the panel as compared to a normal control;
wherein the set of biomarkers consists of α2 Macroglobulin (A2M), α1 Antitrypsin (α1AT), Angiopoietin 2 (ANG2), Brain derived neurotrophic factor (BDNF), Betacellulin, Bone morphogenic protein 6 (BMP6), Carcinoembryonic Antigen (CEA), CD40 Ligand (CD40L), Cortisol, Connective tissue growth factor (CTGF), Epidermal growth factor (EGF), Eotaxin 3, Factor VII, Follicle stimulating hormone (FSH), GM-CSF, Glutathione S transferase (GST), Haptoglobin (HPT), ICAM 1, IGFBP 2, Interleukin 10 (IL 10), IL 17, IL 5, Luteinizing Hormone (LH), MIF, NrCAM, Pancreatic Polypeptide (PP), Prostatic acid phosphatise (PAP), RANTES (C—C motif chemokine 5), Resistin, SGOT, Sortilin, Stem Cell Factor (SCF), Thrombopoietin (TPO) and Thrombospondin 1 (TSP1).

12. The method of claim 11, wherein the quantifying is performed on two or more occasions.

13. The method of claim 12, wherein the quantifying is performed prior to the administering.

14. The method of claim 12, wherein the quantifying is repeated at intervals throughout the individual's lifetime.

15. The method of claim 11, wherein the administering further comprises at least one therapy selected from the group consisting of psychotherapy, counseling, hospitalization, electroconvulsive therapy, and combinations thereof.

* * * * *

UNITED STATES PATENT AND TRADEMARK OFFICE
CERTIFICATE OF CORRECTION

PATENT NO. : 10,527,632 B2
APPLICATION NO. : 13/995848
DATED : January 7, 2020
INVENTOR(S) : Bahn et al.

Page 1 of 1

It is certified that error appears in the above-identified patent and that said Letters Patent is hereby corrected as shown below:

In the Claims

Column 21, Line 31, please delete the word "and"

Column 21, Line 46, please insert the word --and-- at the end of this line

Column 22, Line 32, please insert the word --and-- at the end of this line

Signed and Sealed this
Fourteenth Day of April, 2020

Andrei Iancu
*Director of the United States Patent and Trademark Office*